(12) United States Patent
Kasai et al.

(10) Patent No.: US 6,580,014 B1
(45) Date of Patent: Jun. 17, 2003

(54) ABSORBENT ARTICLE AND THE LIKE

(75) Inventors: Takao Kasai, Haga-gun (JP); Hiroki Minowa, Haga-gun (JP); Taketo Ito, Haga-gun (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/831,269

(22) PCT Filed: Nov. 4, 1999

(86) PCT No.: PCT/JP99/06141
§ 371 (c)(1),
(2), (4) Date: Jul. 3, 2001

(87) PCT Pub. No.: WO00/27443
PCT Pub. Date: May 18, 2000

(30) Foreign Application Priority Data

Nov. 9, 1998 (JP) ............................................. 10-317923
Oct. 21, 1999 (JP) ............................................. 11-299983

(51) Int. Cl.$^7$ ................................................. A61F 13/15
(52) U.S. Cl. .................... 604/368; 604/367; 604/375; 604/378; 604/379
(58) Field of Search ................................ 604/368, 367, 604/375, 378, 379

(56) References Cited

U.S. PATENT DOCUMENTS

| | | | | | |
|---|---|---|---|---|---|
| 4,333,461 A | * | 6/1982 | Muller | ........................ | 604/368 |
| 4,624,868 A | * | 11/1986 | Muller | ..................... | 106/205.3 |
| 5,340,853 A | * | 8/1994 | Chmelir et al. | ................ | 524/54 |
| 5,801,116 A | * | 9/1998 | Cottrell et al. | ............... | 502/401 |

FOREIGN PATENT DOCUMENTS

| | | | | |
|---|---|---|---|---|
| EP | 137608 | * | 4/1985 | ........... A61L/15/00 |
| JP | A3 697450 | | 8/1981 | |
| JP | A60 104503 | | 6/1985 | |
| JP | A1 221575 | | 9/1989 | |
| WO | WO 95/17147 | * | 6/1995 | ........... A61F/13/15 |

* cited by examiner

*Primary Examiner*—John J. Calvert
*Assistant Examiner*—Angela J. Grayson
(74) *Attorney, Agent, or Firm*—Birch, Stewart, Kolasch & Birch, LLP

(57) ABSTRACT

An article (1) for thickening body fluids or excreta which contains a polysaccharide (10) capable of thickening in the presence of a polyvalent metal ion, the polysaccharide (10) being present in a state ready to dissolve or be dissociated in the moisture contained in body fluids or excreta.

10 Claims, 1 Drawing Sheet

ABSORBENT ARTICLE AND THE LIKE

This application is the national phase under 35 U.S.C. §371 of PCT International Application Ser. No. PCT/JP99/06141 which has an International filing date of Nov. 4, 1999, which designated the United States of America and was not published in English.

TECHNICAL FIELD

The present invention relates to an article for thickening body fluids or excreta such as disposable diapers, sanitary napkins, liners for diapers, panty liners and surgical blood absorbent articles, etc. More particularly the present invention relates to an article capable of thickening body fluids or excreta which shows high leakproofing effect against high viscous liquids such as soft feces or blood.

BACKGROUND ART

Absorbent articles such as disposable diapers and sanitary napkins comprises an absorbent member for absorbing waste which has particles of a superabsorbent polymer such as a crosslinked polyacrylic acid salt, dispersed in pulp fiber.

The superabsorbent polymer does not move in the absorbent member. It is not until liquid reaches the position where the polymer exists that the polymer absorbs the liquid and fixes it. Accordingly, when a high viscous liquid having a small rate of permeation and diffusion, such as soft feces or blood, is discharged, it is likely that not all the liquid can arrive at the position where the superabsorbent polymer is, or it takes time for all the liquid to reach the position and be absorbed and fixed thereby. Meanwhile a leak can result. It is a conceivable solution to dispose the superabsorbent polymer near the wearer facing surface of the absorbent article thereby reducing the time required for the liquid to reach. In this case, however, the superabsorbent polymer tends to cause a gel blocking phenomenon which interferes with absorption.

An absorbent article using a cross-linkable swellable polysaccharide as an absorbent in place of a superabsorbent polymer is proposed in WO 95/17147. In this absorbent article, the polysaccharide is used in the form of particles which are bound to the surface of a solid substance or incorporated into the substrate matrix so that it may absorb liquid even under pressure and exhibit improved liquid retentivity for an extended period of time. Similarly to the superabsorbent polymer, the bound or incorporated polysaccharide itself does not diffuse in liquid waste but waits for liquid to come. It does not display absorbing and fixing effects until liquid reaches. Therefore, the above-mentioned absorbent article does not have sufficient leakproofness against high viscous liquids similarly to the conventional ones using superabsorbent articles.

DISCLOSURE OF THE INVENTION

Accordingly, an object of the present invention is to provide an article capable of thickening body fluids or excreta which is highly effective in preventing leaks particularly of a high viscous liquid, such as soft feces or blood.

Another object of the present invention is to provide an article capable of thickening body fluids or excreta which is particularly useful as a disposable diaper or a liner for a diaper worn by newborn babies or infants who get rid of soft feces frequently, a sanitary napkin or a panty liner.

The inventors of the present invention have found that the above objects are accomplished by incorporating a specific polysaccharide in a specific state and utilizing the thickening effect of the polysaccharide.

The present invention has been completed based on the above finding. The present invention accomplishes the above objects by providing an article for thickening body fluids or excreta which contains a polysaccharide capable of thickening in the presence of a polyvalent metal ion, the polysaccharide being present in a state ready to dissolve or be dissociated in the moisture contained in body fluids or excreta.

BEST MODE FOR CARRYING OUT THE INVENTION

A preferred embodiment of the article for thickening body fluids or excreta (hereinafter simply referred to as a thickening article) according to the present invention will be described below with reference to a disposable diaper as an example and to the accompanying drawings.

Figure 1:
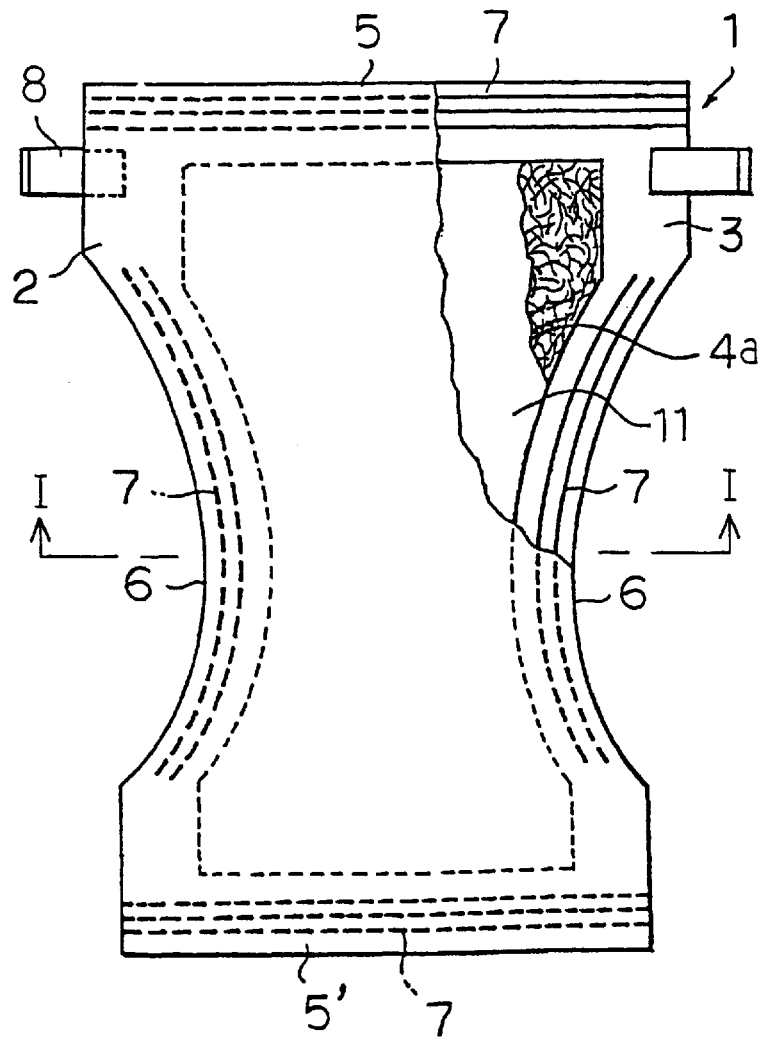
FIG. 1 is a plan view of a disposable diaper as an embodiment of the thickening article of the present invention with a part cut away, seen from its topsheet side.
Figure 2:
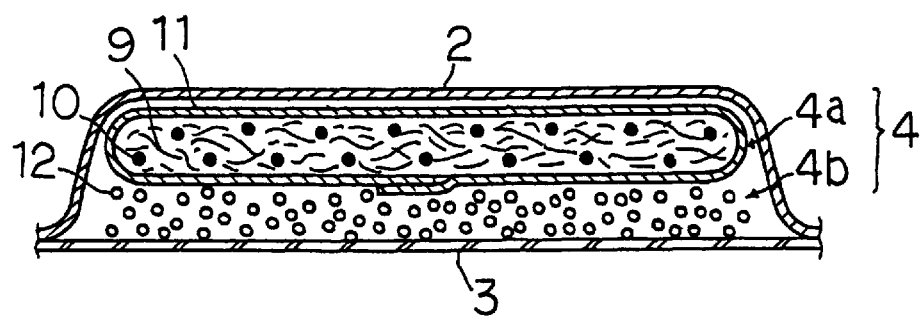
FIG. 2 is an enlarged cross-section of FIG. 1 taken along line I—I.

As shown in FIGS. 1 and 2, the disposable diaper 1 of the embodiment comprises a liquid permeable topsheet 2 which is made of nonwoven fabric, a perforated film, etc.; a liquid impermeable backsheet 3 which serves as a leakproof layer; and a liquid retentive absorbent member 4 which is interposed between the topsheet 2 and the backsheet 3 as an absorbing layer. The absorbent member 4 has its portion corresponding to the crotch portion of the diaper 1 curved inward to form a sandglass shape. The topsheet 2 and the backsheet 3 also have their portion corresponding to the crotch portion of the diaper 1 curved inward in conformity to the shape of the absorbent member 4. The absorbent member 4 is held and fixed between the topsheet 2 and the backsheet 3.

The topsheet 2 and the backsheet 3 extend outward from the front and the rear ends and the lateral sides of the absorbent member 4 to form a front and a rear waist portion 5' and 5 and a pair of leg portions 6 and 6. The front and the rear waist portions 5' and 5 and the pair of leg portions 6 and 6 are each provided with elastically stretchable members 7 for giving the waist portions 5 and 5' and the leg portions 6 and 6 a good fit to a wearer's body when put on the wearer. The stretchable members 7 are fixed by the topsheet 2 and the backsheet 3. A pair of fastening members 8, such as sets of tape fasteners, are attached to both lateral sides of the rear waist portion 5. While not shown, a mating member, such as a rectangular landing tape, is provided on the backsheet 3 in the front waist portion 5'. On putting the disposable diaper 1 of the embodiment on a wearer, the fastening members 8 are stuck on this mating member. The above-mentioned constitution and structure are the same as in conventional disposable diapers.

In the disposable diaper 1 according to this embodiment, the absorbent member 4 has a double-layered structure having an upper absorbent member 4a and a lower absorbent member 4b as shown in FIG. 2. The upper absorbent member 4a predominantly comprises pulp fiber 9. A polysaccharide powder 10 capable of thickening in the presence of a polyvalent metal ion is dispersed uniformly throughout the upper absorbent member 4a in planar and thickness directions. They are wrapped in thin absorbent paper 11, e.g., tissue, to form the upper absorbent member 4a. The lower absorbent member 4b comprises pulp fiber (not shown) having superabsorbent polymer particles 12 dispersed and mixed uniformly. As will be obvious from Examples given later, the lower absorbent member 4b can consist solely of the superabsorbent polymer particles 12.

As a result of the present inventors' study, it has been revealed that incorporation of the above-described polysaccharide into the disposable diaper 1 brings about an enhanced effect against leaks of a highly viscous liquid, such as soft feces or blood. The reasons for this effect enhancement are assumed to be as follows. As previously noted, a superabsorbent polymer used in an absorbent member of conventional disposable diapers, sanitary napkins, etc. does not migrate in the absorbent member and cannot exert its absorbing and fixing performance until a liquid comes to. That is, its absorption and fixation mechanism is, so to speak, passive. On the other hand, the polysaccharide exhibits a liquid fixing effect through gelation similarly to the superabsorbent polymer. Additionally, the polysaccharide is capable of dissolving or being dissociated in water and diffusing in water. So, once liquid waste and the polysaccharide meet, the part of the liquid that is in contact with the polysaccharide is fixed, while the polysaccharide diffuses in the liquid through dissolution or dissociation so that the part of the liquid that is distant from the polysaccharide can also be fixed. In other words, the polysaccharide has, so to speak, a positive mechanism of absorption and fixation. Therefore, even when a high viscous liquid cannot completely get to the position where the polysaccharide is, the polysaccharide is capable of fixing the high viscous liquid. Besides, in the present invention the polysaccharide reacts with trace amounts of polyvalent metal ions present in body fluids or excreta (e.g., calcium ions and aluminum ions) to form complexes having increased viscosity, which come into contact with liquid waste and, as a result, thicken the liquid to develop a fixing effect. Such properties of the polysaccharide enhance the leakproofing effect against high viscous liquids such as soft feces and blood as well as low viscous liquids such as urine. Additionally, since the polysaccharide does not cause gel blocking, it is possible to dispose it near the wearer facing surface of a disposable diaper, a sanitary napkin, etc.

The polysaccharide to be used is one capable of thickening in the presence of a polyvalent metal ion. It is required for the polysaccharide, upon contact with a small amount of a high viscous liquid (moisture), to be dissolved or dissociated and diffused quickly in the high viscous liquid thereby to fix the high viscous liquid. Accordingly, it is preferred for the polysaccharide to contain no polyvalent metal ions. Further, it is preferred for the thickening article of the present invention to contain no polyvalent metal ions. In the practice, however, cases are sometimes met with in which a trace amount of polyvalent metal ions enters unavoidably in the preparation of the polysaccharide, the production of the thickening article or the preparation of members constituting the thickening article. Hence, the situation in which the polysaccharide or the thickening article contains "no polyvalent metal ions" includes cases where they are completely free from either polyvalent metal ions or substances capable of generating polyvalent metal ions in water and cases where polyvalent metal ions or substances capable of generating polyvalent metal ions in water have been unavoidably incorporated in such small amounts that do not interfere with development of thickening to a degree enough to produce a leakproofing effect.

The polysaccharides which contain no polyvalent metal ions include polysaccharides in their free form not forming a metal salt and polysaccharides in their salt form with a monovalent metal ion. The polysaccharides which are not in a metal salt form include pectin, gellan gum, κ-carrageenan, glucomannan, guar gum, casein, and propylene glycol alginate. The polysaccharides in a salt form with a monovalent metal ion include sodium alginate. From the standpoint of cost and water solubility, preferred polysaccharides are pectin, sodium alginate, gellan gum, κ-carrageenan, and the like.

Since the polysaccharide positively dissolves and diffuses in a discharged liquid to thicken the liquid as described above, it is soluble in water or capable of being dissociated in water. The term "capable of being dissociated in water" as used herein means that the polysaccharide does not completely dissolve in water but is ready to be dispersed in water, i.e., it can exist in water with its molecular chains entangled. The term "completely dissolve in water" means that all the molecules of the polysaccharide are individually hydrated.

In the present invention the polysaccharide is required to react sensitively with a discharged liquid to thicken the liquid. Therefore, it is necessary that the polysaccharide should be present in the thickening article in a state ready to dissolve or be dissociated in water. This is totally different from the technique of WO95/17147 supra in which the polysaccharide is incorporated into the matrix of an absorbent article to fix liquid. The "state ready to dissolve or be dissociated in water" includes a state in which a powdered polysaccharide is dispersed in the absorbent member as shown in FIGS. 1 and 2 or a state in which the powder is sprinkled on the upper surface (wearer facing surface) of the absorbent member.

In order to adequately control the thickening rate of the polysaccharide, the physical properties of the gel formed by thickening, and the like, the degree of esterification of the polysaccharide can be adjusted, or the pH can be adjusted by addition of an organic acid, etc.

The polysaccharide can be used in a powdered form as noted above or in a particulate form. It can be encapsulated in water-soluble capsules. When used in the form of powder or particle, a preferred size is 10 to 1000 $\mu$m, particularly 50 to 500 $\mu$m. When used in the form of capsules, a preferred size of the capsules is 300 to 2000 $\mu$m, particularly 500 to 1000 $\mu$m.

The polysaccharide is preferably used in an amount of 10 to 200 g/m$^2$, particularly 30 to 100 g/m$^2$, from the standpoint of cost and the thickening ability (leakproofing effect). The weight ratio of the polysaccharide to the pulp fiber (polysaccharide/pulp fiber) is preferably 10/1000 to 200/50, particularly 1/5 to 1/1. The pulp fiber is preferably used in an amount of 50 to 1000 g/m$^2$, particularly 50 to 300 g/m$^2$.

Taking into consideration the balance with the amounts of the polysaccharide and the pulp fiber in the upper absorbent member 4a, the amount of the superabsorbent polymer in the lower absorbent member 4b is preferably 0 to 500 g/m$^2$, particularly 50 to 300 g/m$^2$.

The position of the polysaccharide in the diaper 1 is not limited to that in the above-described embodiment. For example, the polysaccharide can be disposed in a layer between the upper absorbent layer 4a and the topsheet 2 instead of being incorporated into the upper absorbent member 4a. It can be held in the topsheet 2 or the absorbent paper 11 by means of a prescribed means, such as coating. It can be disposed in the leg portions 6 and 6 or the waist portions 5 and 5', or in, if necessary, the three-dimensional gathers optionally formed on both sides of the diaper 1. Wherever the polysaccharide may be, it can exist either uniformly or in a prescribed pattern, such as lines, checks, dots, etc.

While the thickening article of the present invention has been described with reference to its preferred embodiment, the present invention is not construed as being limited thereto, and various changes and modifications can be made therein without departing from the spirit and scope thereof.

For example, the diaper 1 of the above-described embodiment does not always need to contain the superabsorbent polymer. In this case, not containing hardly degradable substances unlike conventional diapers, the absorbent member is biodegradable, and the diaper 1 as a whole can be made virtually biodegradable by making the topsheet 2 and the backsheet 3 of a biodegradable material.

The polysaccharide can be disposed either on the entire area for liquid absorption or in a specific area of the diaper 1.

The absorbent member 4 can be a single layer. In this case, the amount of the polysaccharide in the portion nearer to the wearer facing surface of the absorbent member is increased relatively to produce the same effect as obtained from the absorbent member having a double-layered structure.

As far as the effects of the present invention are not impaired, the polysaccharide can be used in combination with an antimicrobials, antiseptics, or antifungals. The antimicrobials include benzethonium chloride and benzalkonium chloride. The antiseptics include parahydroxybenzoates (e.g., ethyl p-hydroxybenzoate and methyl p-hydroxybenzoate). Growth of microorganisms during storage can be prevented in the presence of these additives. pH Buffers, antiinflammatory agents, lipase inhibitors or urease inhibitors can also be used in combination to suppress a diaper rash caused particularly by soft feces.

The thickening article of the present invention is applicable to not only disposable diapers but other sanitary articles having an absorbent member, i.e., sanitary napkins, incontinence pads, nursing breast pads, etc.; sanitary articles having no absorbent member, i.e., diaper liners and panty liners; and surgical blood absorbent articles such as dressing; and the like.

EXAMPLE 1

A mixture of fluff pulp and pectin powder (particle size: 150 μm) was built up on absorbent paper (tissue) and enveloped in the absorbent paper to form an upper absorbent layer. The basis weight of the fluff pulp was 50 g/m$^2$, and that of the pectin powder was 50 g/m$^2$. Particles of a superabsorbent polymer were scattered on a polyethylene sheet as a backsheet to give a basis weight of 200 g/m$^2$ to form a lower absorbent layer. The upper absorbent layer was superposed on the lower absorbent layer, and a topsheet made of suction heat-bonded nonwoven fabric of polypropylene fiber was further superposed thereon. The backsheet and the topsheet were joined and fixed together at their periphery with elastically stretchable members interposed therebetween at the periphery to obtain a disposable diaper shown in FIGS. 1 and 2. The disposable diaper (including the pectin powder) contained substantially no polyvalent metal ions.

EXAMPLE 2

A disposable diaper was obtained in the same manner as in Example 1, except that the pectin powder was not used in the upper absorbent layer but sprinkled between the upper absorbent layer and the topsheet in an amount of 50 g/m$^2$.

EXAMPLE 3

A disposable diaper was obtained in the same manner as in Example 1, except that the pectin powder was not used in the upper absorbent layer but sprinkled on the topsheet which had been sprinkled with water in an amount of 50 g/m$^2$ and fixed thereto by its own adhesion.

EXAMPLES 4 TO 6

A disposable diaper was obtained in the same manner as in Example 1, except for replacing the pectin used in Example 1 with sodium alginate (Example 4), gellan gum (Example 5) or κ-carrageenan (Example 6).

COMPARATIVE EXAMPLE 1

A disposable diaper was obtained in the same manner as in Example 1, except that particles of a superabsorbent polymer were incorporated into the upper absorbent layer in place of the pectin powder used in Example 1.

Evaluation of Performance:

In order to evaluate the performance of the disposable diapers obtained in Examples and Comparative Example, a leakage test was carried out in accordance with the following method. Further, the thickening effect of the polysaccharides used in Examples 1 and 4 to 6 was evaluated in a thickening test according to the following method. The results obtained are shown in Table 1.

Leakage Test:

Thirty diapers for each Example were used by each of ten babies under 12 months. The number of diapers which had a leak was divided by the total number of diapers used was taken as a leak ratio for evaluating leakproofness.

Leak ratio (%)=[(number of diaper having a leak)/(total number of used diapers)]×100

Thickening Test:

Each of the polysaccharides used in Examples 1 and 4 to 6 was added to 500 ml of an aqueous calcium chloride solution having a calcium ion content of 0.1% by weight to become a concentration of 0.2% by weight. The kinematic viscosity (20° C.) of the aqueous solution was measured with a B-type viscometer (Model B8M, supplied by Tokyo Keiki) before and after addition of the polysaccharide. The measurement after the addition of the polysaccharide was made after 30 seconds from the addition. Even if heterogeneous gelation took place, the measurement was carried out.

TABLE 1

| | Leakage Test Result | Kinematic Viscosity (mm$^2$/s) | |
|---|---|---|---|
| | (%) | Before Addition | After Addition |
| Example 1 | 1.7 | 30 | 82 |
| Example 2 | 2.3 | 30 | 82 |
| Example 3 | 1.3 | 30 | 82 |
| Example 4 | 2.0 | 16 | 96 |
| Example 5 | 1.7 | 10 | 70 |
| Example 6 | 1.7 | 25 | 90 |
| Comparative Example 1 | 6.3 | — | — |

As is apparent from the results shown in Table 1, it is seen that the diapers of Examples which contained the polysaccharide (the articles of the present invention) exhibit higher leakproofness against a high viscous liquid than the diaper of Comparative Example which contained no polysaccharide.

INDUSTRIAL APPLICABILITY

The present invention provides a thickening article having high leakproofness against high viscous liquids such as soft feces and blood.

The thickening article of the present invention is useful as a disposable diaper or a diaper liner which is worn particularly by newborn babies or infants who get rid of soft feces frequently, a sanitary napkins, a panty liner, an incontinence pad, a nursing breast pad, a surgical blood absorbent article, and so forth.

What is claimed is:

1. An article for thickening body fluids or excreta which contains a polysaccharide capable of reacting with a polyvalent metal ion to form a complex and thickening, said polysaccharide being present in a state ready to dissolve or be dissociated in the moisture contained in body fluids or excreta.

2. The article for thickening body fluids or excreta as claimed in claim 1, which comprises a liquid retentive absorbent layer.

3. The article for thickening body fluids or excreta as claimed in claim 1, wherein said polysaccharide contains no polyvalent metal ions.

4. The article for thickening body fluids or excreta as claimed in claim 2, wherein said polysaccharide is present in said absorbent layer which predominantly comprises pulp fiber.

5. The article for thickening body fluids or excreta as claimed in claim 2, wherein said absorbent layer is interposed between a liquid permeable topsheet and a liquid impermeable leakproof layer, and said polysaccharide is disposed between the absorbent layer predominantly comprising pulp fiber and said topsheet.

6. The article for thickening body fluids or excreta as claimed in claim 1, wherein said polysaccharide comprises pectin, gellan gum, κ-carrageenan, glucomannan, guar gum, casein, sodium alginate or propylene glycol alginate.

7. An article for thickening body fluids or excreta comprising:
   A. a liquid-permeable top sheet;
   B. a liquid-impermeable back sheet
   C. a liquid-permeable envelope between the top sheet and the back sheet;
   D. a composition within the envelope, said composition comprising powder of a polysaccharide capable of reacting with a polyvalent metal ion to form a complex and thickening, said polysaccharide being present in a state ready to dissolve or be dissociated in the moisture contained in body fluids or excreta;
   E. a layer of super absorbent polymer particles within the diaper between the back sheet and the envelope.

8. An article for thickening body fluids or excreta comprising:
   A. a liquid-permeable top sheet;
   B. a liquid-impermeable back sheet;
   C. a liquid-permeable envelope between the top sheet and the back sheet;
   D. a composition within the envelope, said composition comprising a mixture of
      1. a powder of a polysaccharide capable of reacting with a polyvalent metal ion to form a complex and thickening, said polysaccharide being present in a state ready to dissolve or be dissociated in the moisture contained in body fluids or excreta wherein said polysaccharide is pectin; and
      2. fibers; and
   E. a layer of super absorbent polymer particles within the diaper between the back sheet and the envelope.

9. An article for thickening body fluids or excreta comprising:
   A. a liquid-permeable top sheet carrying a composition comprising powder of a polysaccharide capable of reacting with a polyvalent metal ion to form a complex and thickening, said polysaccharide being present in a state ready to dissolve or be dissociated in the moisture contained in body fluids or excreta;
   B. a liquid-impermeable back sheet;
   C. an absorbent member carrying super absorbent polymer particles said absorbent member residing between the back sheet and the top sheet.

10. An article for thickening body fluids or excreta comprising:
    A. a liquid-permeable top sheet;
    B. an absorbent member carrying a super absorbent polymer; and
    C. a second member having a first face which faces the top sheet and a second face which faces away from the top sheet; said absorbent member carrying a composition comprising powder of a polysaccharide capable of reacting with a polyvalent metal ion to form a complex and thickening, said polysaccharide being present in a state ready to dissolve or be dissociated in the moisture contained in body fluids or excreta on the face of the second member facing the top sheet.

* * * * *